United States Patent
Chan et al.

(10) Patent No.: US 7,592,487 B2
(45) Date of Patent: Sep. 22, 2009

(54) CHIRAL TERTIARY AMINOALKYLNAPHTHOLS

(75) Inventors: Albert Sun-Chi Chan, Hung Hom (HK); Jianxin Ji, Nashville, TN (US)

(73) Assignee: The Hong Kong Polytechnic University, Kowloon (HK)

( * ) Notice: Subject to any disclaimer, the term of this patent is extended or adjusted under 35 U.S.C. 154(b) by 0 days.

(21) Appl. No.: 10/590,544

(22) PCT Filed: Mar. 10, 2005

(86) PCT No.: PCT/CN2005/000291

§ 371 (c)(1),
(2), (4) Date: Nov. 13, 2006

(87) PCT Pub. No.: WO2005/087707

PCT Pub. Date: Sep. 22, 2005

(65) Prior Publication Data

US 2008/0045757 A1     Feb. 21, 2008

Related U.S. Application Data

(60) Provisional application No. 60/552,785, filed on Mar. 12, 2004.

(51) Int. Cl.
*C07C 211/00*     (2006.01)
*C07C 29/38*     (2006.01)

(52) U.S. Cl. ............................ 564/337; 568/809

(58) Field of Classification Search .................. None
See application file for complete search history.

(56) References Cited

FOREIGN PATENT DOCUMENTS

EP     1671953     6/2006

OTHER PUBLICATIONS

Cimarelli et al, "A practical stereoselective synthesis of secondary and tertiary aminonaphthols: chiral ligands for enantioselective catalysts in the addition of diethylzinc to benzaldehyde"; Tetrahedron: Asymmetry (2002), 13(22), 2417-2426.*

Cimarelli et al. Ready N-Alkylation of enantiopure aminophenols: synthesis of tertiary amino phenols. Tetrahedron, 57, (2001), p. 6086-6096.*

Cimarelli et al., Tetrahedron: Symmetry 13, pp. 2417-2426, A practical stereoselective synthesis of secondary and tertiary aminonaphthols: chiral ligands for enantioselective catalysts in the addition of diethylzinc to benzaldehyde (2002).

Da-Xue et al., Organic Letters, vol. 3, No. 17, pp. 2733-2735 The Application of Chiral Aminonaphthols in the Enantioselective Addition of Diethylzinc to Aryl Aldehydes (2001).

Jian-Xin et al., J. Org. Chem., 70, pp. 1093-1095, Highly Enantioselective Phenyl Transfer to Aryl Aldehydes Catalyzed by Easily Accessible Chiral Tertiary Aminonaphthol (2005).

Jian-Xin et al., J. Org. chem.., 68, pp. 1589-1590, A Convenient, One-Step Synthesis of Optically Active Tertiary Aminonaphthol and its Applications in the Highly Enantioselective Alkenylations of Aldehydes (2003).

Wang, Yi et al: "Synthesis of a new type of chiral amino phosphine ligands for asymmetric catalysis", Database CA [Online} Chemical Abstracts Service, Columbus, Ohio, retrieved from STN Database accession No. 2002:585040 and Tetrahedron: Asymmetry, 13(12), 1291-1297 Coden: Tasye3; ISSN: 0957-4166, 2002.

* cited by examiner

*Primary Examiner*—Sikarl A Witherspoon
(74) *Attorney, Agent, or Firm*—Sandra Shim; John Kung

(57) ABSTRACT

The invention relates to the compounds of formula: (I) which are as defined in the specification. Their use as chiral ligands in catalytic aryl transfer reactions to aromatic aldehydes is also described.

21 Claims, No Drawings

CHIRAL TERTIARY AMINOALKYLNAPHTHOLS

This application claims benefit of U.S. Provisional Application 60/552,785, filed Mar. 12, 2004.

BACKGROUND OF THE INVENTION

Asymmetric catalysis is one of the most powerful methods for accessing a wide range of enantiomerically enriched compounds through the action of a chiral catalyst in a variety of asymmetric reactions. In the last few years, catalytic asymmetric alkylation of carbonyl compounds, especially aldehydes, has achieved substantial interest due to employment of organozinc reagents in the presence of a variety of chiral ligands such as β-amino alcohols, amino thiols and pyridyl alcohols (review by Pu and Yu, *Chem. Rev.* 2001, 101, 757-824). Such asymmetric organozinc additions allow the synthesis of many chiral alcohols that are valuable precursors for the manufacture of pharmacologically and biologically active compounds.

More recently, a practical application of easily accessible chiral secondary and tertiary aminoalkylnaphthols in asymmetric addition of diethylzinc to aromatic aldehydes has been reported by Liu et al., *Org. Lett.* 2001, 3, 2733-2735, and by Palmieri et al., *Tetrahedron: Asymmetry* 2002, 13, 2417-2426. Similarly, a convenient protocol for the asymmetric alkenylation of aldehydes employing a tertiary aminoalkylnaphthol ligand has been described by Chan et al., *J. Org. Chemistry* 2003, 68, 1589-1590.

However, compared to the well established enantioselective alkylations of aldehydes, the corresponding aryl transfer reactions have not yet reached a high level of utility. Up to now, ligands which have been successfully applied to catalyze aryl transfer reactions with high enantiomeric excess (ee) are relatively rare and difficult to manufacture, e.g., catalysts based upon ligands with planar chirality such as the ferrocene derivative shown below.

Thus, the development of other types of effective chiral ligands is an important challenge in the area of catalytic aryl transfer reactions, in particular, chiral ligands which are highly selective and synthetically easily accessible.

SUMMARY OF THE INVENTION

The present invention relates to compounds of the formula (I)

wherein
$R_1$ is optionally substituted lower alkyl or aralkyl;
$R_2$ is optionally substituted lower alkyl;
$R_3$ and $R_4$ are independently hydrogen, halo, lower alkyl, alkoxy or trifluoromethyl; or
$R_3$ and $R_4$ combined together with the carbon atoms to which they are attached form an optionally substituted fused 6-membered aromatic ring provided that $R_3$ and $R_4$ are attached to carbon atoms adjacent to each other;
$R_5$ is hydrogen, lower alkyl, lower alkoxy or halo;
$R_6$ and $R_7$ are hydrogen; or
$R_6$ and $R_7$ combined together with the carbon atoms to which they are attached form a fused 6-membered aromatic ring;

provided that
(i) $R_3$, $R_4$, $R_5$, $R_6$ and $R_7$ are not hydrogen when $R_1$ is methyl, ethyl, pentyl, allyl, 3-buten-1-yl, benzyl or phenethyl and $R_2$ is methyl; or
(ii) $R_3$, $R_4$, $R_6$ and $R_7$ are not hydrogen when $R_1$ and $R_2$ are methyl and $R_5$ is methyl located at the 4-position;

or an enantiomer thereof; or an enantiomeric mixture thereof.

The compounds of formula (I) are chiral tertiary aminoalkylnaphthols and may be employed as chiral ligands in asymmetric catalysis of organozinc additions to carbonyl compounds, in particular, in catalytic aryl transfer reactions to aromatic aldehydes. The compounds of the present invention are easily accessible in high diastereomeric and enantiomeric purity according to the methods disclosed herein.

Other objects, features, advantages and aspects of the present invention will become apparent to those skilled in the art from the following description and appended claims. It should be understood, however, that the following description, appended claims, and specific examples, while indicating preferred embodiments of the invention, are given by way of illustration only. Various changes and modifications within the spirit and scope of the disclosed invention will become readily apparent to those skilled in the art from reading the following.

DETAILED DESCRIPTION OF THE INVENTION

Listed below are definitions of various terms used to describe the compounds of the present invention. These definitions apply to the terms as they are used throughout the specification unless they are otherwise limited in specific instances either individually or as part of a larger group.

The term "optionally substituted alkyl" refers to unsubstituted or substituted straight- or branched-chain hydrocarbon groups having 1-20 carbon atoms, preferably 1-7 carbon atoms. Exemplary unsubstituted alkyl groups include methyl, ethyl, propyl, isopropyl, n-butyl, t-butyl, isobutyl, pentyl, neopentyl, hexyl, isohexyl, heptyl, octyl and the like. Substituted alkyl groups include, but are not limited to, alkyl groups substituted by one or more of the following groups: halo, hydroxy, alkoxy, carboxy, amino, alkylamino, dialkylamino, cycloalkyl, alkenyl, or heterocyclyl.

The term "lower alkyl" refers to those optionally substituted alkyl groups as described above having 1-7, preferably 1-4 carbon atoms.

The term "alkoxy" refers to optionally substituted alkyl-O—.

The term "alkenyl" refers to any of the above alkyl groups having at least two carbon atoms and further containing a carbon to carbon double bond at the point of attachment. Groups having 2 to 4 carbon atoms are preferred.

The term "halogen", "halide" or "halo" refers to fluorine, chlorine, bromine and iodine.

The term "cycloalkyl" refers to optionally substituted monocyclic aliphatic hydrocarbon groups of 3-6 carbon atoms, which may be substituted by one or more substituents, such as alkyl, alkoxy or halo.

Exemplary monocyclic hydrocarbon groups include, but are not limited to, cyclopropyl, cyclobutyl, cyclopentyl, cyclohexyl and the like.

The terms "alkylamino" and "dialkylamino" refer to alkyl-NH— and (alkyl)$_2$N—, respectively.

The term "aryl" refers to a phenyl group, which may optionally be substituted by 1-4 substituents, such as optionally substituted alkyl, cycloalkyl, halo or alkoxy.

The term "aralkyl" refers to an aryl group bonded directly through an alkyl group, such as benzyl or phenethyl.

The term "heterocyclyl" or "heterocyclo" refers to an optionally substituted, fully saturated or unsaturated, aromatic or non-aromatic cyclic group, for example, which is a 4- to 7-membered monocyclic, 7- to 12-membered bicyclic, or 10- to 15-membered tricyclic ring system, which has at least one heteroatom in at least one carbon atom containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, triazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups substituted with 1, 2 or 3 substituents selected from the group consisting of:

(a) alkyl;
(b) hydroxy;
(c) halo;
(d) oxo (i.e. =O);
(e) amino, alkylamino or dialkylamino;
(f) alkoxy;

-continued (g) cycloalkyl;
(h) nitro;
(i) alkylthio; and
(j) aryl substituted with alkyl, cycloalkyl, alkoxy, hydroxy, amino, alkylamino, dialkylamino or halo.

As described herein above, the present invention relates to compounds of formula (I), to methods for their preparation, and to use of such compounds in asymmetric catalysis. Compounds of the present invention are particularly useful when employed as chiral ligands in asymmetric catalysis of organozinc additions to carbonyl compounds. The compounds of formula (I) are particularly useful as chiral ligands in catalytic enantioselective aryl transfer reactions to aromatic aldehydes.

When required, protecting groups may be introduced to protect the functional groups present from undesired reactions with reaction components under the conditions used for carrying out a particular chemical transformation of the present invention. The need and choice of protecting groups for a particular reaction is known to those skilled in the art and depends on the nature of the functional group to be protected (amino, hydroxy etc.), the structure and stability of the molecule of which the substituent is a part and the reaction conditions.

Well-known protecting groups that meet these conditions and their introduction and removal are described, for example, in McOmie, "*Protective Groups in Organic Chemistry*", Plenum Press, London, NY (1973); Greene and Wuts, "*Protective Groups in Organic Synthesis*", John Wiley and Sons, Inc., NY (1999).

Preferred are compounds of formula (I) wherein $R_3$ and $R_4$ combined together with the carbon atoms to which they are attached form an optionally substituted fused 6-membered aromatic ring provided that $R_3$ and $R_4$ are attached to carbon atoms adjacent to each other;

or an enantiomer thereof; or an enantiomeric mixture thereof.

Further preferred are the compounds of formula (I) having the formula

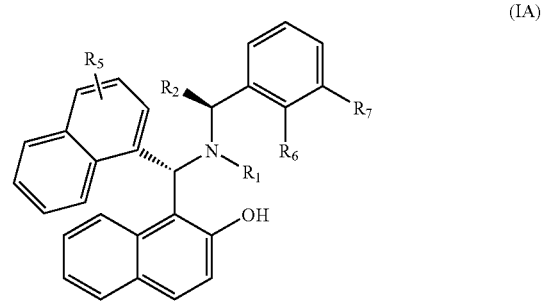

(IA)

wherein $R_1$ is optionally substituted $C_{1-4}$alkyl;
$R_2$ is methyl;
$R_5$ is hydrogen;
$R_6$ and $R_7$ are hydrogen; or
$R_6$ and $R_7$ combined together with the carbon atoms to which they are attached form a fused 6-membered aromatic ring;

or an enantiomer thereof; or an enantiomeric mixture thereof.

Preferred are the compounds of formula (IA) wherein
R$_6$ and R$_7$ are hydrogen;

or an enantiomer thereof; or an enantiomeric mixture thereof.

Further preferred are the compounds of formula (IA) wherein
R$_1$ is methyl;

or an enantiomer thereof; or an enantiomeric mixture thereof.

The compounds of the present invention preferably have an optical purity of at least 90% ee, more preferably at least 95% ee, and most preferably at least 98% ee.

The compounds of formula (I) may be prepared as described by Palmieri et al., *Tetrahedron: Asymmetry* 2002, 13, 2417-2426. Alternatively, the compounds of formula (I) may be obtained by a highly stereoselective one-step, three component Mannich-type reaction as described by Chan et al., *J. Org. Chemistry* 2003, 68, 1589-1590. For example, an aldehyde of the formula

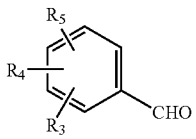

(II)

wherein R$_3$ and R$_4$ are independently hydrogen, halo, lower alkyl, alkoxy or trifluoromethyl; or R$_3$ and R$_4$ combined together with the carbon atoms to which they are attached form an optionally substituted fused 6-membered aromatic ring provided that R$_3$ and R$_4$ are attached to carbon atoms adjacent to each other; and R$_5$ is hydrogen, lower alkyl, lower alkoxy or halo; may be condensed simultaneously with a naphthol of the formula

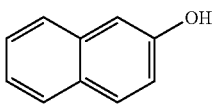

(III)

and an amine of the formula

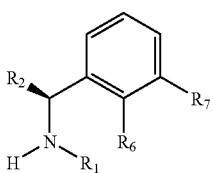

(IV)

wherein R$_1$ is optionally substituted lower alkyl or aralkyl; R$_2$ is optionally substituted lower alkyl; and R$_6$ and R$_7$ are hydrogen; or R$_6$ and R$_7$ combined together with the carbon atoms to which they are attached form a fused 6-membered aromatic ring; or an enantiomer thereof; or an enantiomeric mixture thereof; to afford a compound of formula (I) wherein R$_1$, R$_2$, R$_3$, R$_4$, R$_5$, R$_6$ and R$_7$ have meanings as defined herein above. Compounds of formula (II) and formula (IV) are known, or if they are novel they may be prepared using methods well known in the art.

As described by Chan et al., *J. Org. Chemistry* 2003, 68, 1589-1590, the above condensation is preferably conducted without an intrinsic solvent at a temperature ranging from room temperature (RT) to about 95° C. to afford compounds of formula (I) exclusively as a single diastereomer. The molar ratio of an aldehyde of formula (II) to a naphthol of formula (III), and the molar ratio an amine of formula (IV) to a naphthol of formula (III) originally present in the reaction mixture preferably ranges from about 0.5:1 to about 2:1 and from about 0.5:1.to about 2:1, respectively. A compound of formula (I) may then be isolated as a single stereoisomer by simply adding a lower alcohol, preferably methanol (MeOH), to the crude reaction mixture to initiate precipitation of the product which may be used as such without further purification in the following organozinc additions. The operational simplicity involved, as well as the inexpensive reagents make this synthetic methodology suitable for a large-scale preparation.

As described herein above, the compounds of formula (I) are chiral tertiary aminoalkylnaphthols and may be employed as chiral ligands in asymmetric catalysis of organozinc additions to carbonyl compounds. In other words, the present invention provides methods for converting a carbonyl compound to a chiral alcohol in the presence of a suitable organozinc reagent and a compound of the formula

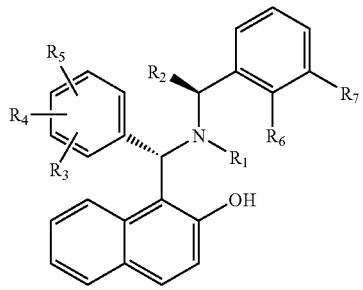

(I)

wherein
R$_1$ is optionally substituted lower alkyl or aralkyl;
R$_2$ is optionally substituted lower alkyl;
R$_3$ and R$_4$ are independently hydrogen, halo, lower alkyl, alkoxy or trifluoromethyl; or
R$_3$ and R$_4$ combined together with the carbon atoms to which they are attached form an optionally substituted fused 6-membered aromatic ring provided that R$_3$ and R$_4$ are attached to carbon atoms adjacent to each other;
R$_5$ is hydrogen, lower alkyl, lower alkoxy or halo;
R$_6$ and R$_7$ are hydrogen; or
R$_6$ and R$_7$ combined together with the carbon atoms to which they are attached form a fused 6-membered aromatic ring;

provided that
(i) R$_3$, R$_4$, R$_5$, R$_6$ and R$_7$ are not hydrogen when R$_1$ is methyl, ethyl, pentyl, allyl, 3-buten-1-yl, benzyl or phenethyl and R$_2$ is methyl; or
(ii) R$_3$, R$_4$, R$_6$ and R$_7$ are not hydrogen when R$_1$ and R$_2$ are methyl and R$_5$ is methyl located at the 4-position;

or an enantiomer thereof; or an enantiomeric mixture thereof.

Effective are the methods of the present invention, wherein
R$_3$ and R$_4$ combined together with the carbon atoms to which they are attached form an optionally substituted fused 6-membered aromatic ring provided that $R_3$ and $R_4$ are attached to carbon atoms adjacent to each other;

or an enantiomer thereof; or an enantiomeric mixture thereof.

Particularly effective are the methods of the present invention, wherein a compound of formula (I) has the formula

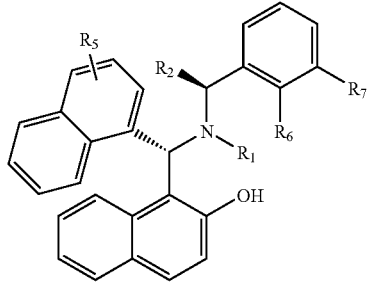

(IA)

wherein
- $R_1$ is optionally substituted $C_{1-4}$alkyl;
- $R_2$ is methyl;
- $R_5$ is hydrogen;
- $R_6$ and $R_7$ are hydrogen; or
- $R_6$ and $R_7$ combined together with the carbon atoms to which they are attached form a fused 6-membered aromatic ring;

or an enantiomer thereof; or an enantiomeric mixture thereof.

Especially effective are the methods of the present invention, wherein
- $R_6$ and $R_7$ are hydrogen;

or an enantiomer thereof; or an enantiomeric mixture thereof.

Advantageous are the methods of the present invention, wherein
- $R_1$ is methyl;

or an enantiomer thereof; or an enantiomeric mixture thereof.

In a particular embodiment of the present invention the carbonyl compound is an aromatic aldehyde which according to the methods of the present invention is converted to a chiral diarylmethanol.

Generally, the organozinc additions, in particular the aryl transfer reactions to aromatic aldehydes, according to the present invention may be carried out in an inert organic solvent such as toluene, hexane, pentane, tetrahydrofuran (THF), or a mixture of solvents thereof. Preferably, the organozinc additions are conducted in toluene at a temperature ranging from about −45° C. to about 40° C. More preferably, the reaction temperature ranges from about −15° C. to about 0° C. The molar ratio of the compound of formula (I) to the carbonyl compound initially present in the reaction mixture ranges preferably from about 0.05:1 to about 0.3:1. More preferably, the molar ratio is about 0.16:1. Preferably, the molar ratio of the organozinc reagent to the carbonyl compound initially present in the reaction mixture is about 2:1.

If desired, the organozinc additions, in particular the aryl transfer reactions to aromatic aldehydes, may be carried out in the presence of a polyether such as dimethoxypolyethylene glycol (DiMPEG). Preferably, the molar ratio of the polyether to the carbonyl compound initially present in the reaction mixture ranges from about 0.05:1 to about 0.2:1. More preferably, the molar ratio is about 0.1:1.

The organozinc reagents applicable to the methods of the present invention are known, or if they are novel they may be prepared using methods well known in the art. For example, as described herein in the illustrative Examples, organozinc reagents may be generated, preferably in situ, by reacting a compound of the formula $$R_8B(OH)_2 \qquad (V)$$

wherein $R_8$ represents aryl; with an excess of dimethyl zinc (ZnMe₂) or diethyl zinc (ZnEt₂) in an inert organic solvent such as toluene, hexane, pentane, THF, or a mixture of solvents thereof. Preferably, the reaction is conducted in toluene at a temperature of about 60° C. for a period of time required to convert a compound of formula (V) to the desired organozinc reagent; e.g., about 10-15 h. The reaction mixture may then be cooled to a temperature ranging from about −15° C. to RT, preferably the reaction mixture is cooled to about 0° C., and then treated with a compound of formula (i). The reaction temperature may be further adjusted as desired prior to addition of the carbonyl compound. Preferably, the carbonyl compound is an aromatic aldehyde which is added to the reaction mixture at about −15° C. The molar ratio of the compound of formula (V) originally present in the reaction mixture to the carbonyl compound subsequently added to the reaction mixture is preferably about 2:1.

The effectiveness of the methods of the present invention is illustrated in Table 1 for asymmetric phenyl transfer reactions to various substituted benzaldehydes catalyzed by a compound of formula (I) having the formula

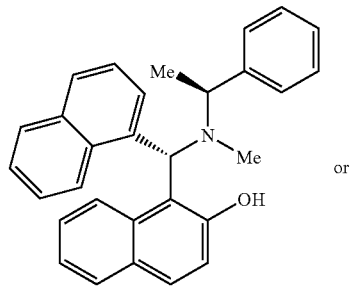

(IB)

or

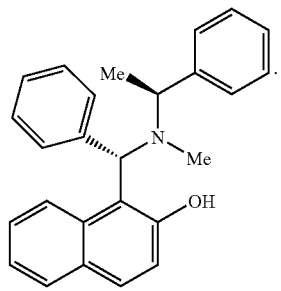

(IC)

A number of chiral diarylmethanol may be produced in high ee values and chemical yields. In most cases, the compound of formula (IB) as the catalyst (Methods A and C) demonstrates higher enantioselectivities than the compound of formula (IC) (Method B). When ZnMe₂ (Method C) in toluene is used to generate the phenyl transfer reagent with phenylboronic acid (PhB(OH)₂) instead of ZnEt₂ (Method A), similar ee values are obtained but with lower chemical yields under otherwise identical reaction conditions (see entries 8 and 11). For ortho-substituted benzaldehydes, a catalyst loading of 8 mol % of (IB) is sufficient to achieve the same level of ee in comparison with that obtained using 16 mol % of (IB) (see entries 2 and 1). Interestingly, different from the trends that have been previously reported in the art, ortho-substituted benzaldehydes are obtainable in higher ee values than other substrates under the catalysis of (IB).

As the data in Table 1 illustrates, compounds of formula (I) may be employed as highly efficient chiral ligands in asymmetric phenyl transfer reactions. Furthermore, the simple synthetic protocol applicable to the preparation of compounds of formula (I) provides an excellent opportunity for large-scale applications.

TABLE 1

Catalytic Asymmetric Phenyl Transfer to Aromatic Aldehydes[a]

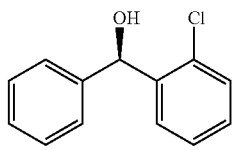

PhB(OH)$_2$/ZnEt$_2$, DiMPEG (10 mol %)
catalyst (IB) or (IC)

Toluene, −15° C., 15 h

| entry | R | cat., mol % | yield (%)[b] | ee (%)[c] | config.[d] |
|---|---|---|---|---|---|
| 1 | o-Cl | (IB), 16 | 92.5 | 97.3 | R |
| 2 | o-Cl | (IB), 8 | 91.1 | 96.9 | R |
| 3 | o-Cl | (IC), 8 | 91.3 | 94.3 | R |
| 4 | o-F | (IB), 8 | 92.6 | 97.2 | R |
| 5 | o-Br | (IB), 8 | 89.8 | 96.7 | R |
| 6 | o-Br | (IC), 8 | 90.2 | 95.3 | R |
| 7 | o-OMe | (IB), 8 | 93.4 | 96.1 | R |
| 8[e] | o-OMe | (IB), 8 | 86.6 | 97.0 | R |
| 9 | o-OMe | (IC), 8 | 92.7 | 94.3 | R |
| 10 | o-Me | (IB), 8 | 93.6 | 98.9 | R |
| 11[e] | o-Me | (IB), 8 | 89.5 | 99.0 | R |
| 12 | o-Me | (IC), 8 | 93.1 | 97.1 | R |
| 13 | m-Me | (IB), 16 | 86.5 | 94.6 | R |
| 14 | m-Me | (IC), 16 | 83.4 | 92.1 | R |
| 15 | p-Cl | (IB), 16 | 90.2 | 94.1 | R |
| 16 | p-Cl | (IB), 8 | 88.7 | 91.9 | R |
| 17 | p-Cl | (IC), 8 | 85.2 | 88.4 | R |
| 18 | p-Br | (IB), 16 | 90.1 | 93.7 | R |
| 19 | p-Br | (IC), 16 | 91.6 | 91.1 | R |
| 20 | p-Me | (IB), 16 | 93.2 | 94.3 | R |
| 21 | p-Me | (IC), 16 | 91.5 | 90.5 | R |

[a]2.0 eq. of Ph(OH)$_2$ and 6.5 eq. of ZnEt$_2$ are employed to produce the phenyl transfer reagent as described in the illustrative Examples (Methods A and B).
[b]Isolated yields.
[c]Determined by chiral HPLC analysis.
[d]The absolute configuration is assigned by comparison of the HPLC peak elution order with known data.
[e]ZnMe$_2$ is used instead of ZnEt$_2$ (Method C).

The following Examples are intended to further illustrate the invention and are not to be construed as being limitations thereon. If not mentioned otherwise, all evaporations are performed under reduced pressure, preferably between about 5 and 50 mmHg. The structure of products and starting materials is confirmed by standard analytical methods, e.g., microanalysis, melting point, high pressure liquid chromatography (HPLC) and spectroscopic characteristics, e.g., MS, IR, NMR. Abbreviations used are those conventional in the art.

EXAMPLE 1

1-{(S)-[Methyl-((S)-1-phenyl-ethyl)-amino]-naphthalen-1-yl-methyl}-naphthalen-2-ol

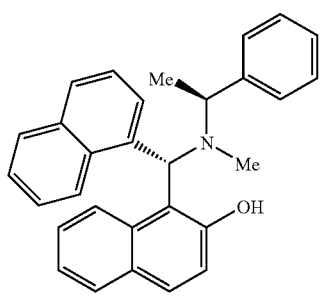

(IB)

1-Naphthaldehyde (2.7 mL, 20 mmol), (S)-(−)-N,α-dimetylbenzylamine (2.60 g, 19 mmol) and 2-naphthol (2.43 g, 16 mmol) are charged into a 25 mL flask with a magnetic stirring bar. The mixture is heated to 85° C. and stirred for 72 h. After the system is cooled to RT, MeOH (5 mL) is added and the precipitated product is collected by filtration, washed with MeOH (5 mL) and dried to afford 1-{(S)-[methyl-((S)-1-phenyl-ethyl)-amino]-naphthalen-1-yl-methyl}-naphthalen-2-ol as white crystals (about 51% yield): $^{1}$H NMR (500 MHz, CDCl$_3$) δ 14.01 (br s, 1H), 7.77-7.02 (m, 18H), 6.45 (s, 1H), 4.40 (br s, 1H), 1.95 (s, 3H), 1.65 (br s, 3H); MS (EI) m/z (rel intensity) 418 (M$^+$+1), 283, 141, 136; HRMS (EI) Calcd for C$_{30}$H$_{28}$NO (M$^+$+1): 418.2171, found 418.2135.

EXAMPLE 2

(Method A)

(R)-(2-Chlorophenyl)phenylmethanol

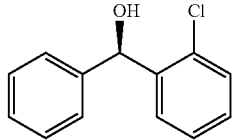

PhB(OH)$_2$ (122 mg, 1.0 mmol) and ZnEt$_2$ (334 μL, 3.25 mmol) in toluene (1 mL) is charged to a 10 mL flask under a nitrogin atmosphere. This mixture is heated to 60° C. and stirred for 10 h with a magnetic stirrer. Then the mixture is cooled to 0° C. and the title compound of Example 1, 1-{(S)-[methyl-((S)-1-phenyl-ethyl)-amino]-naphthalen-1-yl-methyl}-naphthalen-2-ol (16.7 mg, 0.04 mmol) in toluene (0.5 mL) and DiMPEG (100 mg, 0.05 mmol) in toluene (0.5 mL) are added. After stirring for additional 15 min, the solution is cooled to −15° C. and 2-chlorobenzaldehyde (70.0 mg, 0.5 mmol) in toluene (1 mL) is added. After stirring 15 h at −15° C., the reaction is quenched with 1 N hydrochloric acid (HCl, 2 mL) and the mixture is extracted with ethyl acetate (EtOAc, 5 mL), dried over anhydrous sodium sulfate (Na$_2$SO$_4$) and the solvent is removed in vacuo. The purification of the residue by flash chromatography (EtOAc/hexane, 1:10) gives (R)-(2-chlorophenyl)phenylmethanol in about 96.9% ee and about 91.1% yield (the ee value is determined by HPLC using a Chiralcel OB-H column).

EXAMPLE 3

(Method B)

(R)-(2-Chlorophenyl)phenylmethanol

PhB(OH)$_2$ (122 mg, 1.0 mmol) and ZnEt$_2$ (334 μL, 3.25 mmol) in toluene (1 mL) is charged to a 10 mL flask under a nitrogin atmosphere. This mixture is heated to 60° C. and stirred for 10 h with a magnetic stirrer. Then the mixture is cooled to 0° C. and 1-{(S)-[methyl-((S)-1-phenyl-ethyl)-amino]-phenyl-methyl}-naphthalen-2-ol (prepared as described by Chan et al., *J. Org. Chemistry* 2003, 68, 1589-1590; 14.7 mg, 0.04 mmol) in toluene (0.5 mL) and DiMPEG (100 mg, 0.05 mmol) in toluene (0.5 mL) is added. After stirring for additional 15 min, the solution is cooled to −15° C. and 2-chlorobenzaldehyde (70.0 mg, 0.5 mmol) in toluene (1 mL) is added. After stirring 15 h at −15° C., the reaction is quenched with 1 N HCl (2 mL) and the mixture is extracted with EtOAc (5 mL), dried over anhydrous Na$_2$SO$_4$ and the solvent is removed in vacuo. The purification of the residue by flash chromatography (EtOAc/hexane, 1:10) gives (R)-(2-chlorophenyl)-phenylmethanol in about 94.3% ee and about 91.3% yield (the ee value is determined by HPLC using a Chiralcel OD-H column).

EXAMPLE 4

(Method C)

(R)-(2-Chlorophenyl)phenylmethanol

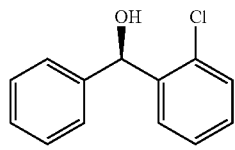

PhB(OH)$_2$ (122 mg, 1.0 mmol) and ZnMe$_2$ (2.0 M solution in toluene, 1.6 mL)) is charged to a 10 mL flask under a nitrogin atmosphere. This mixture is heated to 50° C. and stirred for 8 h with a magnetic stirrer. Then the mixture is cooled to 0° C. and the title compound of Example 1, 1-{(S)-[methyl-((S)-1-phenyl-ethyl)-amino]-naphthalen-1-yl-methyl}-naphthalen-2-ol (16.7 mg, 0.04 mmol) in toluene (0.5 mL) and DiMPEG (100 mg, 0.05 mmol) in toluene (0.5 mL) are added. After stirring for additional 15 min, the solution is cooled to −15° C. and 2-chlorobenzaldehyde (70 mg, 0.5 mmol) in toluene (1 mL) is added. After stirring 15 h at −15° C., the reaction is quenched with 1 N HCl (2 mL) and the mixture is extracted with EtOAc (5 mL), dried over anhydrous Na$_2$SO$_4$ and the solvent is removed in vacuo. The purification of the residue by flash chromatography (EtOAc/hexane, 1:10) gives (R)-(2-chlorophenyl)phenylmethanol in about 97.0% ee and about 86.6% yield (the ee value is determined by HPLC using a Chiralcel OB-H column).

EXAMPLE 5

(R)-(2-Bromophenyl)phenylmethanol

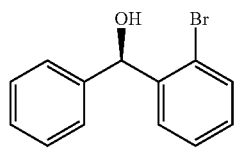

The title compound is prepared according to Method A in about 96.7% ee and about 89.8% yield (the ee value is determined by HPLC using a Chiralcel OD-H column).

EXAMPLE 6

(R)-(2-Fluorophenyl)phenylmethanol

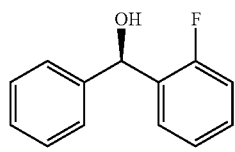

The title compound is prepared according to Method A in about 97.2% ee and about 92.6% yield (the ee value is determined by HPLC using a Chiralcel OD-H column).

EXAMPLE 7

(R)-(2-Tolyl)phenylmethanol

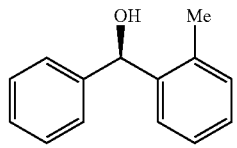

The title compound is prepared according to Method A in about 98.9% ee and 93.6% yield (the ee value is determined by HPLC using a Chiralcel OB-H column).

EXAMPLE 8

(R)-(2-Methoxyphenyl)phenylmethanol

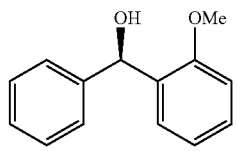

The title compound is prepared according to Method A in about 96.1% ee and about 93.4% yield (the ee value is determined by HPLC using a Chiralcel OB-H column).

EXAMPLE 9

(R)-(3-Tolyl)phenylmethanol

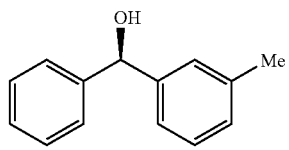

The title compound is prepared according to Method A in about 94.6% ee and about 86.5% yield (the ee is determined by HPLC using a Chiralcel OB-H column).

EXAMPLE 10

(R)-(4-Chlorophenyl)phenylmethanol

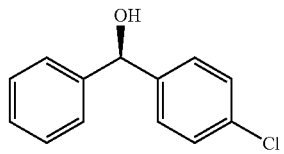

The title compound is prepared according to Method A in about 94.1% ee and about 90.2% yield (the ee is determined by HPLC using a Chiralcel OB-H column).

EXAMPLE 11

(R)-(4-Tolylphenyl)phenylmethanol

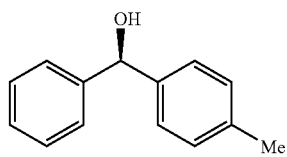

EXAMPLE 12

(R)-(4-Bromophenyl)phenylmethanol

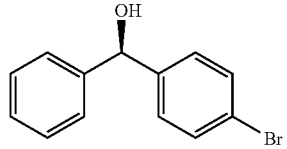

The title compound is prepared according to Method A in about 93.7% ee and about 90.1% yield (the ee is determined by HPLC using a Chiralcel OB-H column).

What is claimed is:

1. A compound of the formula

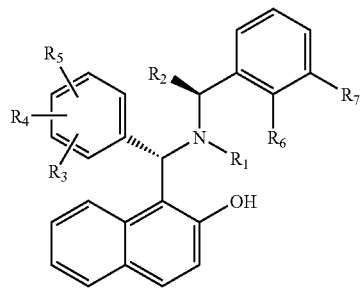

(I)

wherein
 $R_1$ is optionally substituted lower alkyl or aralkyl;
 $R_2$ is optionally substituted lower alkyl;
 $R_3$ and $R_4$ are independently hydrogen, halo, lower alkyl, alkoxy or trifluoromethyl; or
 $R_3$ and $R_4$ combined together with the carbon atoms to which they are attached form an optionally substituted fused 6-membered aromatic ring provided that $R_3$ and $R_4$ are attached to carbon atoms adjacent to each other;
 $R_5$ is hydrogen, lower alkyl, lower alkoxy or halo;
 $R_6$ and $R_7$ are hydrogen; or
 $R_6$ and $R_7$ combined together with the carbon atoms to which they are attached form a fused 6-membered aromatic ring;
provided that
 (i) $R_3$, $R_4$, $R_5$, $R_6$ and $R_7$ are not hydrogen when $R_1$ is methyl, ethyl, pentyl, allyl, 3-buten-1-yl, benzyl or phenethyl and $R_2$ is methyl; or
 (ii) $R_3$, $R_4$, $R_6$ and $R_7$ are not hydrogen when $R_1$ and $R_2$ are methyl and $R_5$ is methyl located at the 4-position;
or an enantiomer thereof; or an enantiomeric mixture thereof.

2. A compound according to claim 1, wherein
 $R_3$ and $R_4$ combined together with the carbon atoms to which they are attached form an optionally substituted fused 6-membered aromatic ring provided that $R_3$ and $R_4$ are attached to carbon atoms adjacent to each other;
or an enantiomer thereof; or an enantiomeric mixture thereof.

3. A compound according to claim 2 of the formula

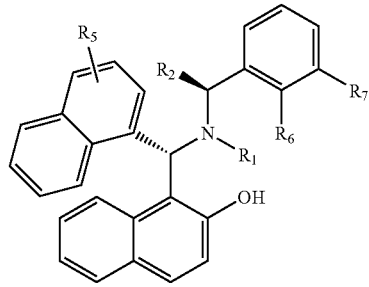

(IA)

wherein
 $R_1$ is optionally substituted $C_{1-4}$alkyl;
 $R_2$ is methyl;
 $R_5$ is hydrogen;
 $R_6$ and $R_7$ are hydrogen; or
 $R_6$ and $R_7$ combined together with the carbon atoms to which they are attached form a fused 6-membered aromatic ring;
or an enantiomer thereof; or an enantiomeric mixture thereof.

4. A compound according to claim 3, wherein
 $R_6$ and $R_7$ are hydrogen;
or an enantiomer thereof; or an enantiomeric mixture thereof.

5. A compound according to claim 4, wherein
 $R_1$ is methyl;
or an enantiomer thereof; or an enantiomeric mixture thereof.

6. A method for converting a carbonyl compound to a chiral alcohol in the presence of a suitable organozinc reagent and a compound of the formula

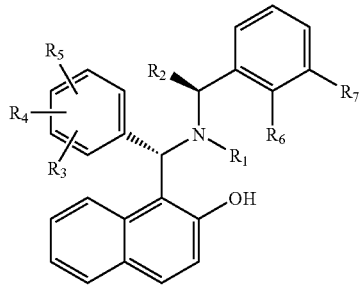

(I)

wherein
 $R_1$ is optionally substituted lower alkyl or aralkyl;
 $R_2$ is optionally substituted lower alkyl;
 $R_3$ and $R_4$ are independently hydrogen, halo, lower alkyl, alkoxy or trifluoromethyl; or
 $R_3$ and $R_4$ combined together with the carbon atoms to which they are attached form an optionally substituted fused 6-membered aromatic ring provided that $R_3$ and $R_4$ are attached to carbon atoms adjacent to each other;
 $R_5$ is hydrogen, lower alkyl, lower alkoxy or halo;
 $R_6$ and $R_7$ are hydrogen; or
 $R_6$ and $R_7$ combined together with the carbon atoms to which they are attached form a fused 6-membered aromatic ring;
provided that
 (i) $R_3$, $R_4$, $R_5$, $R_6$ and $R_7$ are not hydrogen when $R_1$ is methyl, ethyl, pentyl, allyl, 3-buten-1-yl, benzyl or phenethyl and $R_2$ is methyl; or
 (ii) $R_3$, $R_4$, $R_6$ and $R_7$ are not hydrogen when $R_1$ and $R_2$ are methyl and $R_5$ is methyl located at the 4-position;
or an enantiomer thereof; or an enantiomeric mixture thereof.

7. A method according to claim 6, wherein
R$_3$ and R$_4$ combined together with the carbon atoms to which they are attached form an optionally substituted fused 6-membered aromatic ring provided that R$_3$ and R$_4$ are attached to carbon atoms adjacent to each other;
or an enantiomer thereof; or an enantiomeric mixture thereof.

8. A method according to claim 7, wherein a compound of formula (I) has the formula

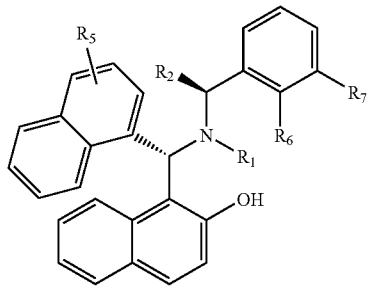

(IA)

wherein
R$_1$ is optionally substituted C$_{1-4}$alkyl;
R$_2$ is methyl;
R$_5$ is hydrogen;
R$_6$ and R$_7$ are hydrogen; or
R$_6$ and R$_7$ combined together with the carbon atoms to which they are attached form a fused 6-membered aromatic ring;
or an enantiomer thereof; or an enantiomeric mixture thereof.

9. A method according to claim 8, wherein
R$_6$ and R$_7$ are hydrogen;
or an enantiomer thereof; or an enantiomeric mixture thereof.

10. A method according to claim 9, wherein
R$_1$ is methyl;
or an enantiomer thereof; or an enantiomeric mixture thereof.

11. A method according to claim 6, wherein the carbonyl compound is an aromatic aldehyde.

12. A method according to claim 11, wherein the chiral alcohol is a diarylmethanol.

13. A method according to claim 12, wherein the organozinc reagent is generated by reacting a compound of the formula $$R_8B(OH)_2 \qquad (V)$$

wherein R$_8$ represents aryl; with dimethyl zinc or diethyl zinc.

14. A method according to claim 12, wherein the reaction mixture further comprises a polyether.

15. A method according to claim 14, wherein the polyether is dimethoxypolyethylene glycol.

16. A method according to claim 12, wherein
R$_3$ and R$_4$ combined together with the carbon atoms to which they are attached form an optionally substituted fused 6-membered aromatic ring provided that R$_3$ and R$_4$ are attached to carbon atoms adjacent to each other;
or an enantiomer thereof; or an enantiomeric mixture thereof.

17. A method according to claim 16, wherein a compound of formula (I) has the formula

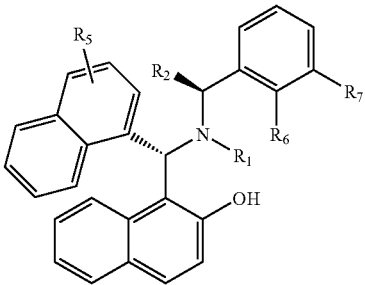

(IA)

wherein
R$_1$ is optionally substituted C$_{1-4}$alkyl;
R$_2$ is methyl;
R$_5$ is hydrogen;
R$_6$ and R$_7$ are hydrogen; or
R$_6$ and R$_7$ combined together with the carbon atoms to which they are attached form a fused 6-membered aromatic ring;
or an enantiomer thereof; or an enantiomeric mixture thereof.

18. A method according to claim 17, wherein
R$_6$ and R$_7$ are hydrogen;
or an enantiomer thereof; or an enantiomeric mixture thereof.

19. A method according to claim 18, wherein
R$_1$ is methyl;
or an enantiomer thereof; or an enantiomeric mixture thereof.

20. A method according to claim 6, wherein the reaction mixture further comprises a polyether.

21. A method according to claim 18, wherein the polyether is dimethoxypolyethylene glycol.

* * * * *